(12) United States Patent
Kirchner et al.

(10) Patent No.: US 10,182,825 B2
(45) Date of Patent: Jan. 22, 2019

(54) VENOUS TOURNIQUET

(71) Applicant: KIMETEC GMBH, Ditzingen (DE)

(72) Inventors: Hansjörg Kirchner, Markgröningen (DE); Claudia Kirchner, Markgröningen (DE); Caroline Ihle, Markgröningen (DE)

(73) Assignee: KIMETEC GMBH, Ditzingen (DE)

( * ) Notice: Subject to any disclaimer, the term of this patent is extended or adjusted under 35 U.S.C. 154(b) by 78 days.

(21) Appl. No.: 15/037,018

(22) PCT Filed: May 6, 2014

(86) PCT No.: PCT/EP2014/059199
§ 371 (c)(1),
(2) Date: May 16, 2016

(87) PCT Pub. No.: WO2015/070992
PCT Pub. Date: May 21, 2015

(65) Prior Publication Data
US 2016/0287262 A1    Oct. 6, 2016

(30) Foreign Application Priority Data
Nov. 15, 2013    (DE) .................. 10 2013 112 597

(51) Int. Cl.
*A61B 17/132* (2006.01)
*A61B 17/00* (2006.01)
*A61B 90/00* (2016.01)

(52) U.S. Cl.
CPC ........ *A61B 17/132* (2013.01); *A61B 17/1322* (2013.01); *A61B 2017/00862* (2013.01); *A61B 2090/037* (2016.02); *A61B 2090/064* (2016.02); *A61B 2090/0807* (2016.02)

(58) Field of Classification Search
CPC .............. A61B 17/132; A61B 17/1322; A61B 2017/00862
See application file for complete search history.

(56) References Cited

U.S. PATENT DOCUMENTS

| 3,586,001 | A |   | 6/1971  | Sanderson |            |
|-----------|---|---|---------|-----------|------------|
| 3,628,536 | A |   | 12/1971 | Glesne    |            |
| 3,930,506 | A |   | 1/1976  | Overend   |            |
| 4,273,130 | A | * | 6/1981  | Simpson   | A61B 17/1322 |
|           |   |   |         |           | 128/DIG. 15 |

(Continued)

FOREIGN PATENT DOCUMENTS

| DE | 10 2009 025 416 A1 | 12/2010 |
|----|-----|---------|
| DE | 20 2013 100 312 U1 | 3/2013 |

(Continued)

*Primary Examiner* — Julie A Szpira
(74) *Attorney, Agent, or Firm* — Pauley Erickson & Kottis

(57) ABSTRACT

A venous tourniquet having a constricting strap which can be placed around a body part, which strap is elastic in the direction of circumference or is provided with at least one elastic portion, and having a closing device by which the constricting strap can be locked into a tightening loop when the strap is positioned around a body part in the tightened state. One embodiment is advantageous if both structure and use is obtained by designing the closing device as a hook-and-loop fastener having two lockingly engaging closing parts.

18 Claims, 4 Drawing Sheets

(56) References Cited

U.S. PATENT DOCUMENTS

| | | | |
|---|---|---|---|
| 4,384,583 A * | 5/1983 | Speelman | A61B 17/1322 2/338 |
| 4,390,014 A * | 6/1983 | Forman | A61F 13/143 2/338 |
| 5,015,251 A * | 5/1991 | Cherubini | A44B 18/0003 128/DIG. 15 |
| 5,036,838 A * | 8/1991 | Sherman | A61F 13/06 128/DIG. 15 |
| D322,854 S | 12/1991 | Campbell | |
| D373,750 S | 9/1996 | Gunderson | |
| D381,427 S | 7/1997 | Marrero | |
| 5,653,728 A | 8/1997 | Ahern et al. | |
| 5,690,672 A * | 11/1997 | Cohen | A61B 5/02233 606/203 |
| 6,050,967 A * | 4/2000 | Walker | A61F 13/00059 602/75 |
| 6,250,047 B1 | 6/2001 | Ahern et al. | |
| 6,525,238 B2 | 2/2003 | Corrales | |
| D639,438 S * | 6/2011 | George | D24/169 |
| 9,242,590 B2 * | 1/2016 | Preston | B60P 7/0823 |
| 9,795,391 B2 * | 10/2017 | Saatchi | A61B 17/1325 |
| 2005/0131322 A1 * | 6/2005 | Harris, Jr. | A61F 5/0104 602/19 |
| 2005/0273134 A1 | 12/2005 | Esposito | |
| 2008/0188889 A1 * | 8/2008 | Dedo | A61B 17/1322 606/203 |
| 2008/0312682 A1 | 12/2008 | Shams et al. | |
| 2009/0062843 A1 * | 3/2009 | Heston | A61B 17/135 606/203 |
| 2012/0071917 A1 | 3/2012 | McDonald et al. | |
| 2012/0122365 A1 * | 5/2012 | Erickson | B32B 5/026 442/312 |
| 2012/0310273 A1 * | 12/2012 | Thorpe | A61B 17/1322 606/203 |
| 2014/0135819 A1 | 5/2014 | Brown | |

FOREIGN PATENT DOCUMENTS

| | | |
|---|---|---|
| EP | 2 045 047 A2 | 4/2009 |
| GB | 479442 A | 2/1938 |
| GB | 1033130 A | 6/1966 |
| GB | 2 424 189 A | 9/2008 |
| WO | WO 2006/015987 A1 | 2/2006 |
| WO | WO 2008/076820 A2 | 6/2008 |

* cited by examiner

FIG. 1A
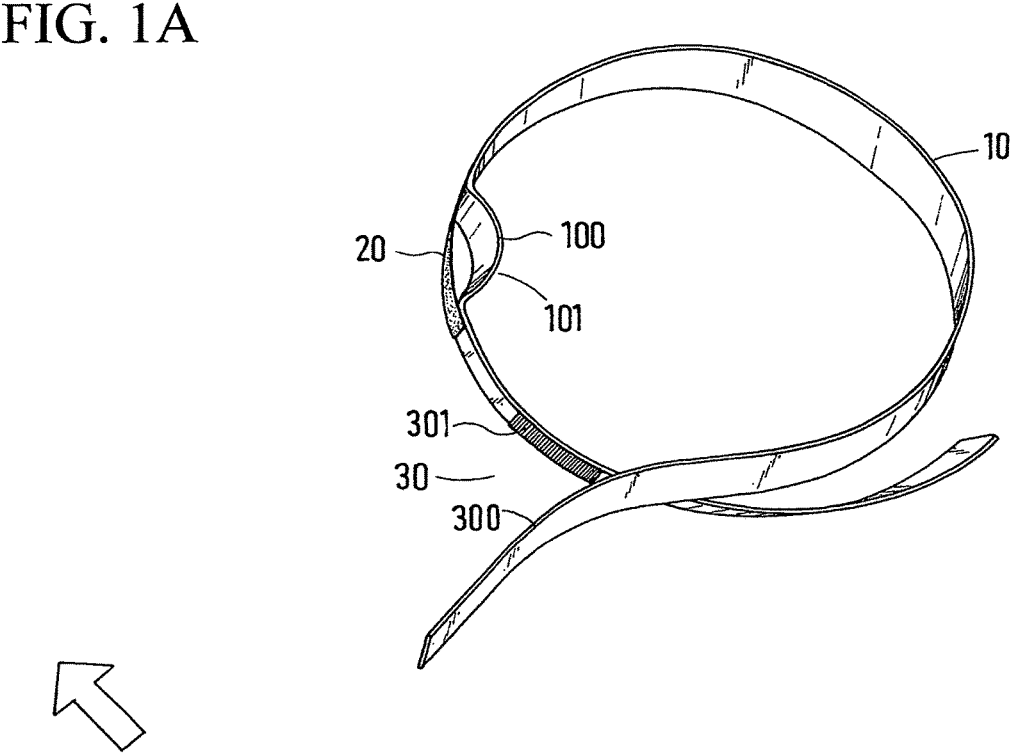
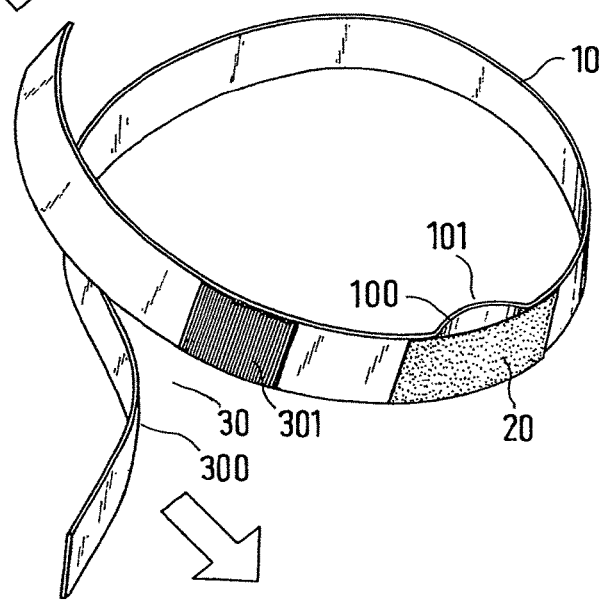
FIG. 1B

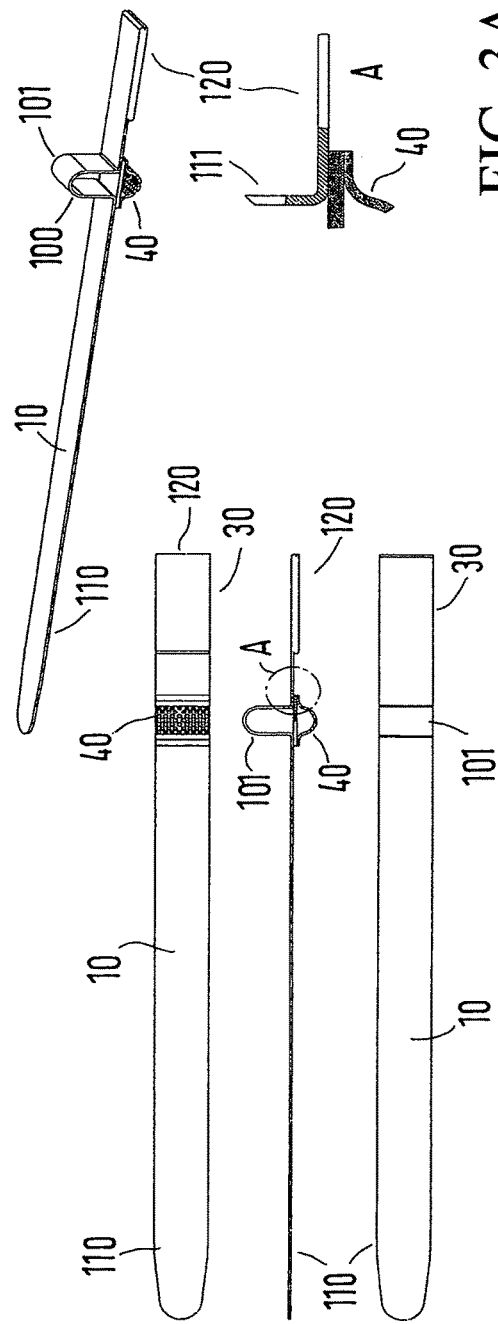
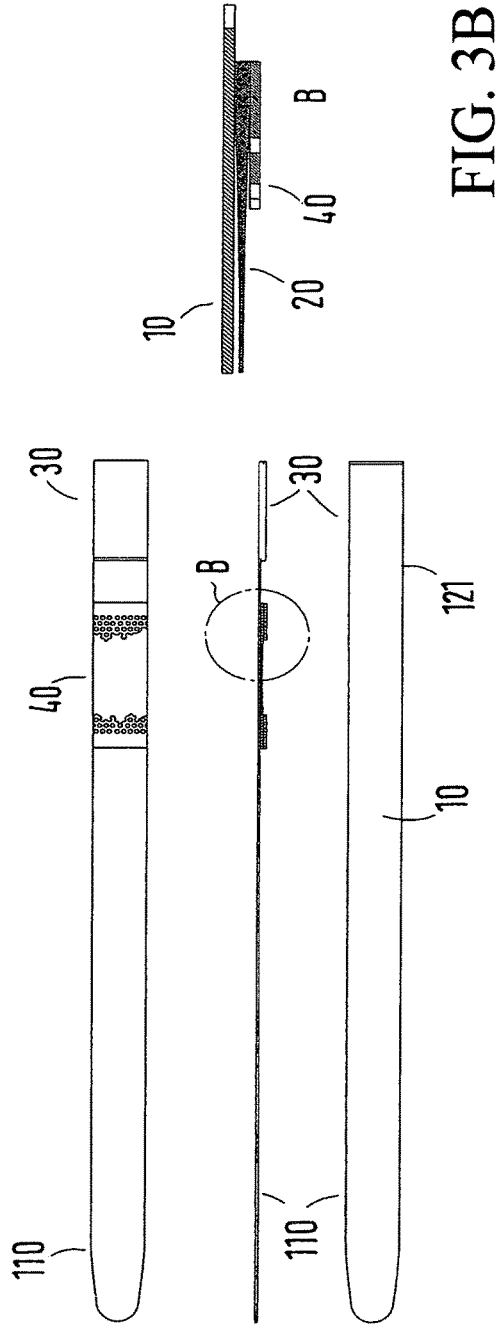
FIG. 3A
FIG. 3B

VENOUS TOURNIQUET

BACKGROUND OF THE INVENTION

Field of the Invention

This invention relates to a venous tourniquet, having a constricting strap that can be placed around a body part and that itself is embodied elastically in a circumferential direction or is provided with at least one elastic portion, and having a closure device by which the constricting strap can be locked in a state in which it is wrapped tightly around a body part, to form a tightening loop.

Discussion of Related Art

One venous tourniquet is disclosed by U.S. Pat. No. 3,930,506. An adhesive portion is applied to an end portion of the constricting strap, for fixation of a tensing loop wrapped around the body part with tensile stress. If this portion is not fixed in the correct position in the first fixation, then reliably fixing it again is not ensured, which can have disadvantages in terms of use. Applying the adhesive also entails corresponding effort.

U.S. Pat. No. 3,628,536 discloses another venous tourniquet that has a closure device with openings, distributed over a length, and with a protrusion attached to one end, which protrusion is adapted to engage openings.

US Patent Application Publication 2012/0071917 A1 discloses a constricting strap device for body parts for preventing severe blood loss in injuries. In this known constricting strap device, a tightening device for attaining high tension of the constricting strap, wrapped into a loop around the body part, and a tension indicator are provided, with which tension indicator a tension of the constricting strap that is generated can be ascertained either in tactile fashion or visually. For example, as shown in FIGS. 14A and 14B and the specification of this document, a tension cloth is folded and fixed in the folded area at fastening locations, which tear if the tension is excessive. The fastening locations can have variously many fastening points over the width of the tension cloth, as a result of which the fastening locations tear if the tensile stress differs accordingly. In any case, a tensile stress this high must not be applied until in order to cause tearing at the fastening location or locations, after which the tensile stress abruptly drops. With these provisions, a metered tension, of the kind that is effective in venous tourniquets, for instance, in order to occlude a venous blood flow, is difficult to achieve and detect. Also, the closure device is relatively complicated.

Further constricting strap devices for body parts are shown in U.S. Pat. No. 5,653,728 A, WO 2006/015987 A1, GB 2 424 189 A, U.S. Pat. No. 6,525,238 B2, US Published Application 2008/0312682 A1, and U.S. Pat. No. 6,250,047 B1. The constricting strap devices are provided with various closure devices, and the locking or fixation is sometimes inconvenient, or the construction is complicated. For example, in U.S. Pat. No. 5,653,728 A and WO 2006/015987 A1, versions of constricting strap devices are also disclosed that can be thrown away after use, of the kind often needed in clinical use for compliance with hygiene regulations.

DE 10 2009 025 416 B4 discloses a supporting or fixation belt with at least one flexible, inelastic portion and fixation devices for fastening belt regions to one another or to orthopedic devices. The fixation devices can be embodied as hook-and-loop closure elements and stitched on, glued, or welded on, or sewn onto ends of a belt strap. The top side of a continuous elastic belt portion can also be equipped with a plush layer, while on the underside, fixation devices for fixing the end regions to one another or to the orthopedic devices are provided. This kind of support or fixation belt with fixation devices in its end regions is not adjustable to variable loop sizes and cannot be used as a venous tourniquet.

Further bandlike belts or belt portions with hook-and-loop closure are shown in EP 2 045 047 A2, GB 479 442 A, and GB 1 033 130 A.

SUMMARY OF THE INVENTION

One object of this invention is to provide a venous tourniquet of the type described above but which is simple in construction, functions securely, and is easier to use.

This object and others are attained with features of this invention as described in this specification and in the claims. The closure device of this invention is embodied as a hook-and-loop closure with two closure parts engaging one another in a locking fashion. The construction provides simple manipulation with only a few gestures in fastening it to the body part, in particular an arm, with sufficient tensile stress, for instance for occluding a vein. Advantageously, the constricting strap device can be used as a disposable item in order to meet hygienic requirements. The two closure parts, preferably with hook elements on one side and loops on the other side, provide a stable connection with tensile strength in the superficial or circumferential direction of the body part.

An especially advantageous construction for production and simple use is obtained if a first closure part is formed of the band material of the constricting strap itself, and a second closure part is formed of a portion of material secured to the band material, or the first and the second closure parts are integrated with the band material.

One advantageous embodiment in terms of function and use is that that the constricting strap is made from plushlike, tear-resistant material with high tensile strength.

A further advantageous embodiment of this invention is obtained if the constricting strap is made from a nonwoven, such as spunbond fabric, felt, or paperlike material with a roughened surface or a surface having fine hairs. The felt can be produced, for example using water-jet hardening.

Various other advantageous embodiments are achieved if the constricting strap is made from polyester, polypropylene and/or viscose material.

For the function and use it is also advantageous if the constricting strap and the second closure part have the same width, in a range from 1 cm to 4 cm, preferably between 1.5 cm and 3 cm.

Further advantages for use are obtained if there is at least one tension indicator for determining a state of tension of the constricting strap, which is embodied so that a defined state of tension is apparent to a user.

With these provisions, the user, for instance in an embodiment of the constricting strap device as a venous tourniquet, can adjust the relatively slight tensile stress required to suppress blood flow (for example, ca. 10 mm Hg in the vicinity of capillaries or <25 mm Hg in the vicinity of larger veins) exactly. As a result, the person being treated is also not stressed any more than necessary.

In an advantageous embodiment for detecting the tensile stress generated is that the tension indicator is embodied as an elastic portion on the constricting strap in the stretching direction between two fixation points, having a strap portion embodied of a flexible, inelastic material and spanning a defined excess length relative to the unstressed constricting strap. If the strap portion embodied with an excess length with respect to the spacing of the fixation points in the untensed state of the constricting strap (for example, as a folded portion) is still loose, then a defined, predetermined tension state is not yet reached. Conversely, if the flexible inelastic strap portion extends all the way along the constricting strap, because the elastic portion is stretched between the fixation points, then the defined tension state, for example for suppressing the venous blood flow, is attained. With the excess length of the strap portion between the two fixation points, a desired defined tension state for a given application can thus be specified by the manufacturer, which tension state is easily and unambiguously detectable and adjustable in use by the user.

In one advantageous embodiment of this invention, the constricting strap is embodied of a flexible inelastic material, and the strap portion forms an integral part of the constricting strap, and an elastic element forming the elastic portion is attached at the fixation points.

In another advantageous embodiment of this invention, the constricting strap itself is embodied at least in some portions as an elastic portion, and the strap portion of inelastic material is attached to the elastic portion at the fixation points.

A constricting strap device that is advantageous as a disposable item if the elastic portion or a different portion of the elastic strap is provided with a usage indicator, for instance of paper or lacquer, that tears or is damaged when stretching first occurs. The tearing force of the usage indicator is advantageously low, so that it affects the tension method of the constricting strap as little as possible, and the tear ensues for example already at low elongation of a few percent of the elongation at the defined tension state, for example, no more than 10% or 20% of the elongation in the defined tension state. This can be attained for example with a suitable material selection and/or material thickness and/or shape of the usage indicator or by tearing off at an attachment point.

The provisions by which the attachment is brought about by securing the second closure part and optionally the elastic portion or the strap portion to the constricting strap at the fixation points by gluing, welding, thermoplastic methods, or stitching are advantageous from the standpoint of both manufacturing and function.

BRIEF DESCRIPTION OF THE DRAWINGS

This invention is described in view of exemplary embodiments with reference to the drawings, wherein:

FIGS. 1A and 1B show a first embodiment of this invention for a constricting strap device in two different perspective views;

FIGS. 3A and 3B show a further embodiment of this invention of the constricting strap device in the untensed state of the constricting strap and in the tensed state thereof in a top view, a side view, a view from the bottom, and a perspective view, as well as enlarged detail views in both states.

DETAILED DESCRIPTION OF THE INVENTION

Figure 2:
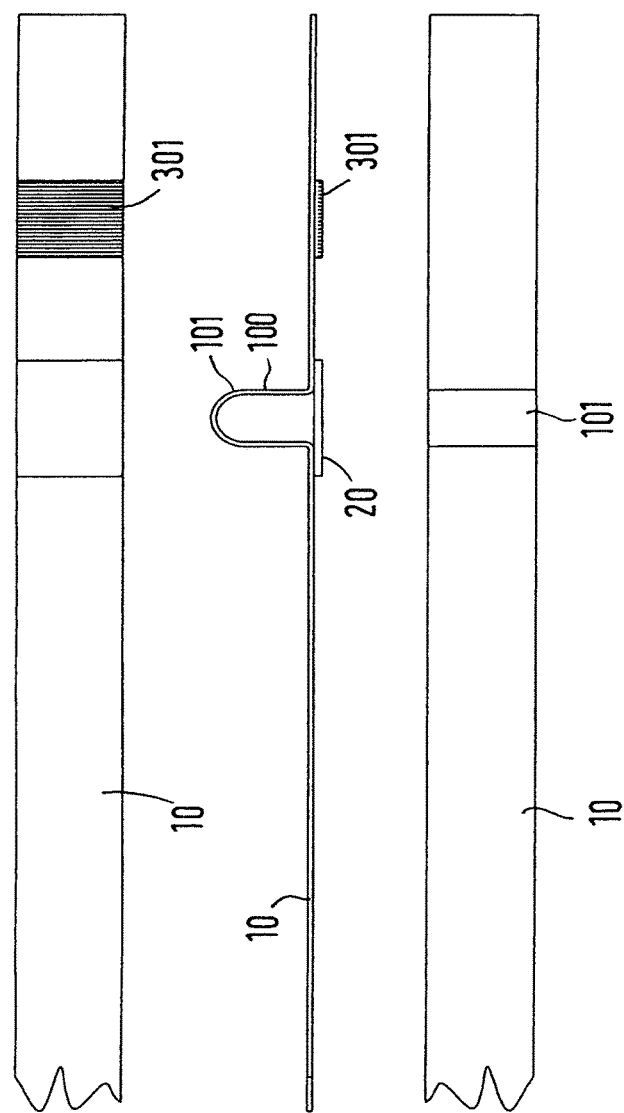
FIG. 2 shows the constricting strap device of FIG. 1A in a top view, a side view, and a view from below.

FIGS. 1A and 1B show a first exemplary embodiment for a constricting strap device 1, embodied as a venous tourniquet, having a constricting strap 10 that for at least partially suppressing blood flow can be wrapped in the form of a closed tension loop around a body part and in the tensed state can be fixed with or by means of a closure device 30. The closure device 30 is embodied as a hook-and-loop closure with two closure parts engaging one another in a locking fashion, such as a first closure part 300 and a second closure part 301.

In the exemplary embodiment shown, the constricting strap device 1 has a tension indicator 101, with which the tensing force of the constricting strap 10, in the vicinity of or near the tension loop wrapped around a body part, can be detected by a user. The tension indicator 101 is preferably located in the vicinity of or near the closure-side band portion, so that in every case it is subject to the tensing force exerted by the tensing loop on the body part to which it is applied.

In the exemplary embodiment shown in FIGS. 1A and 1B, the constricting strap 10 itself is embodied as a first closure part 300 of the closure device 30, while the second closure part 301 is embodied as a portion of material secured to the constricting strap 10. An advantageous aspect is that the constricting strap 10 is made from a plush material that is sufficiently tear-proof or has sufficiently strong tensile strength with respect to the incident elongation forces, which forms loops (slings) for the hook-and-loop closure, while the second closure part 301 is embodied as a short portion of flat material with hook elements adapted to the loops of the first closure part 300.

The hook elements preferably have tiny hooks directed counter to the tensile force or tension force of the band portion wrapped around the applicable body part; however, they may also be embodied in the shape of mushroom caps, flakelike elements, or the like; and the loops, or the sling cloth containing them, are adapted accordingly. In particular, the loops, which need not necessarily be embodied as closed loops, and the hook elements can catch on another in a miniaturized embodiment in the form of many tiny hairs, producing a kind of gecko effect. Advantageously, the loops and hook elements of the two closure parts are embodied as microelements, in such a way that the constricting strap feels soft, even when it is in direct contact with the skin on a body part that is to be constricted.

In studies, it has been found that the hook-and-loop closure embodied in the aforementioned way, in the applied state, absorbs sufficiently strong tensile forces (shear forces) parallel to the surface or in the circumferential direction of the constricting strap 10 to ensure the requisite tying off, for instance of veins, and a tension state of the constricting strap 10 for generating a pressure of up to 10 mm Hg, for example, or up to 25 mm Hg in the vicinity of or near the veins can be reliably achieved. For applying and removal, the hook-and-loop closure can be closed and opened easily and quickly.

The constricting strap 10 which for example is between 1 and 5 cm wide (preferably between 1.5 cm and 3 cm) can be cut from very thin (less than 1 mm) of rolled or two-dimensional material and is very flexible while having a relatively high tear strength. It can itself have for example a slight intrinsic elasticity, so that after being applied to the body part, it generates an elastic tension force on its own. Alternatively or in addition, the tension force can be generated by an elastic element 20, made from a suitable material. This element is secured to the constricting strap 10 in the vicinity of or near the tension indicator 101, or outside the tension indicator.

The second closure part 301 advantageously has the same width as the constricting strap 10 and preferably a slight length, for example between 1 cm and 5 cm. Alternatively, it can also extend over the entire or nearly an entire length of the constricting strap 10. The second closure part 301 is in turn made from thin, flexible material and is secured, for instance by welding (laser welding, ultrasonic welding, or the like), gluing, thermoplastic joining methods, stitching or the like in an end portion of the constricting strap 10 or over the entire or nearly the entire length of the constricting strap. For locking or closing the hook-and-loop closure, the other loop portion placed around the body part needs merely to be pressed against the closure part 301, whereupon the closure parts lock one inside the other. In a further variant embodiment, the loops (or slings) are integrated with one another in the same layer of the nonwoven material or sling cloth.

Suitable materials for the constricting strap or the hook-and-loop closure are viscose, polyester, polypropylene, and advantageously spunbond fabric is used, in a version that is kind or gentle to the skin.

FIG. 2 shows a portion of the constricting strap device, embodied as a venous tourniquet, with the constricting strap 10, a tension indicator 101 with an elongation portion 100, and a spanning elastic element as well as a second closure part 301 of the hook-and-loop closure, in a plan view, a side view, and a view from below.

In FIG. 3A, the constricting strap device 1, embodied as a venous tourniquet, is shown in a top view, a side view, and a view from below in the untensed state. In FIG. 3B, the constricting strap device or venous tourniquet is shown in a tensed state of the constricting strap 10, also with an enlarged detail B in the vicinity of the tension indicator 101. The constricting strap 10 has stretched by a defined length in the vicinity of an elongation portion 100, in which an elastic element 20 is located. As soon as this defined distance, beginning in the untensed state of the constricting strap 10, or a less-tensed state, is reached, a defined tension state of the constricting strap 10 exists. The tensing force effected can be adjusted with or by means of a suitable choice of material (material properties and/or geometric properties, such as length, thickness, width, recesses, or the like) in manufacture in a defined way. In FIGS. 3A and 3B, a usage indicator 40, described in further detail hereinafter, is also shown.

In the exemplary embodiment shown, the constricting strap 10 itself can be made from inelastic, but flexible material. When the constricting strap device 1 is manufactured in rolls, it can be stored or kept on hand and cut to the desired length of the constricting strap 10. Advantageously, a recyclable material can be selected, including with natural reinforcement fibers, for instance, from renewable resources, can be incorporated, and the parts, such as the closure device, elongation portion, fasteners or fastening means, and the like can be chosen taking good recyclability into account. The production, mode of operation and design of the constricting strap device 1 can advantageously also be oriented toward a disposable device.

The tension indicator 101, in the exemplary embodiment shown in FIGS. 1A and 1B, is embodied for instance as part of an essentially inelastic constricting strap 10 itself, in that it is attached with excess length at two fixation points, spaced apart from one another in the elongation direction, to the elongation portion 100 which is of elastic material. Between the two fixation points, the constricting strap 10 there forming the tension indicator 101 is in folded form, and the excess length is adapted to the desired defined tension state to be generated, including as a function of the embodiment of the elongation portion 100. The attachment to the fixation points is done firmly enough, for instance by gluing, welding (laser welding, ultrasonic welding or the like), thermoplastic joining methods, stitching, or the like. In tensing the constricting strap 10, the user can control the elongation action and thus the increased tensing force as the folds come closer and closer to the elongation portion 100 and can unambiguously tell when the strap portion, spanning the two fixation points, of the constricting strap 10 has reached its maximally stretched position. At that moment, the defined tension state that has been established and the optimal tensing force of the constricting strap 10 that has been generated are also reached. For example, if the venous blood flow in the vicinity of or near the capillaries is to be suppressed in the transition region between the arterioles and the venules, a suitably established, defined tension state of approximately 10 mm Hg suffices, and the person being treated experiences little stress. In the vicinity of veins, the blood flow or pulsation can be reached for example with or by means of a tension state of the constricting strap 10 corresponding to a pressure of less than 25 mm Hg. For this or other applications, constricting strap devices 1 embodied in accordance with the aforementioned provisions of this invention can be made available, in which the tension indicator 101 and the elongation portion 100 are adapted exactly to the particular intended use.

In a corresponding way, more than one tension indicator can also be attached, preferably with differently defined tension states.

In another exemplary embodiment of the constricting strap device 1 of this invention, the constricting strap 10 itself can be made of elastic material. If a tension indicator 101 of defined excess length is attached to the constricting strap at fixation points spaced apart from one another in the elongation direction, then this tension indicator advantageously comprises flexible, inelastic material, as in the foregoing exemplary embodiment. If the constricting strap 10 has stretched, the folded strap portion of the tension indicator 101 conforms more and more closely to the outside surface of the constricting strap 10. The excess length of the strap portion is adapted to the spanned portion of the elastic constricting strap, which portion then is equivalent to the elastic element 20 of the foregoing exemplary embodiments, specifically in such a way that when the strap portion is at its full extension, the desired, defined tension state is attained without folds along the applicable portion of the constricting strap 10. In this state, the fixation of the loop is then done by the user with or by means of the hook-and-loop closure, without tensing the constricting strap even more.

A further embodiment of the constricting strap device 1 of this invention is shown in FIGS. 3A and 3B. Here the constricting strap device as in the exemplary embodiment of FIG. 1A is provided with a tension indicator 101, which is a strap portion of excess length relative to the unstressed constricting strap and spans an elastic element 20 between two fixation points, as described in further detail above. The closure device 30 as well is embodied as in the exemplary embodiment of FIG. 1A. In addition, however, there is a usage indicator 40, which in the exemplary embodiment shown likewise spans the elastic element 20, or at least a portion thereof extending longitudinally.

The usage indicator 40 is embodied as a tearing element that extends in the longitudinal direction or the elongation direction and that upon elongation of the elastic element 20 tears in response to an only slight expenditure of force before the final elongation is attained, an elongation that is present in the defined tension state. Similarly to the tearing element, another element meant to be irreversibly damaged, such as a lacquer, can be applied. The region in which the tearing element is intended to tear during the elongation process can likewise be determined by a certain excess length between two fixation points or fastening points of the tearing element at the elastic element 20. The excess length of the tearing element, however, is less than the excess length of the strap portion intended for the tension indicator 101. For example, it can be determined in this way that the tearing element will already tear if the elongation of the elastic element has reached, for instance, approximately ca. 20%, ca. 50% or ca. 80%, or some other small intermediate value, relative to the elongation that exists at the defined tension state. In this way, arbitrary intermediate values for tearing can be established exactly. Once the tearing element of the usage indicator 40 has torn, this means that the constricting strap device 1 has already been used beforehand and thus is not being used for the first time, as is necessary with constricting strap devices 1 that are meant to be used only once. The tearing element can for instance comprise an easily tearing paper strip or fiber strip and is preferably inelastic, yet flexible.

If the fixation points of the tension indicator 101 and the fastening points of the usage indicator 40 in plan view coincide, then both indicators can be produced simply in a single common work step and can also be adapted to one another exactly as a functional unit in the desired way.

Binding the tearing element used for the usage indicator 40 at the applicable fixation points or fastening points can be done in a corresponding way to that described in conjunction with the elastic element 20, such as by gluing, welding (laser welding, ultrasonic welding, imprinting with or by means of printing technology, or the like), stitching, or a thermoplastic joining technique, or some other suitable type of fastening. In the enlarged view of detail A, a joining portion (fastening point) is shown in which the elastic element 20 is fixed on its top side to the constricting strap 10 and is joined on its underside with the applicable fastening portion of the tearing element.

In FIG. 3B, the elongated state of the constricting strap 10 is shown, as it is for example in the defined tension state. The tearing element of the usage indicator 40 has torn already as a result of the elongation, and the two edges at either side of the tear are spaced apart from one another by a relatively large elongation gap. For example, the tear has already taken place in a correspondingly early stage of the elongation. In the enlarged view of the tearing region (detail B), not only the portion of the tearing element that remains (on the closure side), but also the elastic element 20 that becomes thinner in the elongation, and the stretched strap portion of the tension indicator 101 can be seen.

Figure 4A:
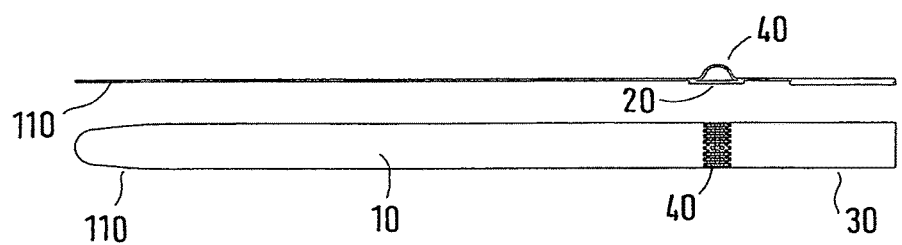
FIGS. 4A and 4B show a further embodiment of this invention for a constricting strap device in the untensed and in the tensed state in a side view and a view from below.
Figure 4B:
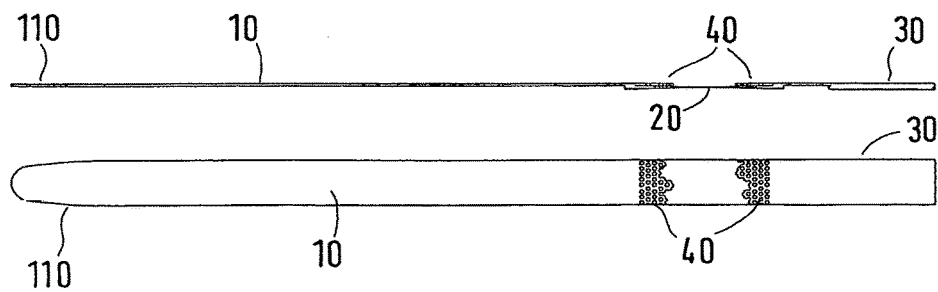

As FIGS. 4A and 4B show, the constricting strap device 1 can also, independently of a tension indicator 101 or offset from it in the longitudinal direction, have a usage indicator 40 on the constricting strap 10 and the usage indicator spans an elastic element 20 between two fixation points or fastening points with (or alternatively without) excess length, similarly to what is described for the version of FIGS. 3A, 3B. The constricting strap 10 can, outside the elastic element 20, again be made of inelastic, flexible material, or of elastic material.

The invention claimed is:
1. A venous tourniquet, comprising:
a constricting strap configured to be placed around a body part, the constricting strap embodied elastically in the circumferential direction or provided with at least one elastic portion, wherein the constricting strap is formed of a plush, tear-resistant nonwoven material with a high tensile strength;
the constricting strap including a closure device configured to lock when the constricting strap is wrapped tightly around the body part, to form a tightening loop, wherein the closure device comprises a hook-and-loop closure with two closure parts engaging one another in locking fashion, a first closure part of the two closure parts being a surface of the nonwoven constricting strap, and a second closure part of the two closure parts being formed of a portion of material secured to the band material, or the first and the second closure parts being integrated with the band material, and wherein the first closure part is provided with loops and the second closure part is provided with hook elements, configured for catching on the loops; and
at least one tension indicator comprising an elongation portion of the constricting strap, wherein the elongation portion is inelastic and indicates a state of tension of the constricting strap in such a way that a defined state of tension is apparent to a user, and wherein the tension indicator the constricting strap is configured to reach a maximally stretched position at a defined tension state corresponding to a pressure of between 10 mm Hg and 25 mm Hg.

2. The venous tourniquet of claim 1, wherein the first closure part has loops and the second closure part has hook elements for catching on the loops.

3. The venous tourniquet of claim 2, wherein the attachment of the second closure part and/or of the elastic portion or of the strap portion, to the constricting strap is brought about at the fixation points by gluing, welding, thermoplastic methods and/or stitching.

4. The venous tourniquet of claim 1, wherein the constricting strap is formed of an inelastic spunbond nonwoven fabric made from a polyester, polypropylene and/or viscose material.

5. The venous tourniquet of claim 4, wherein the constricting strap and the second closure part have a same width in a range from 1 cm to 4 cm.

6. The venous tourniquet of claim 5, wherein the tension indicator is embodied as an elastic portion on the constricting strap in a stretching direction between two fixation points, having a strap portion of a flexible, inelastic material and spanning a defined excess length relative to the unstressed constricting strap.

7. The venous tourniquet of claim 6, wherein the constricting strap is embodied of a flexible inelastic material, and the strap portion forms an integral part of the constricting strap, and an elastic element forming the elastic portion is attached at the fixation points.

8. The venous tourniquet of claim 6, wherein the constricting strap itself is embodied at least in some portions as an elastic portion, and the strap portion of inelastic material is attached to the elastic portion at the fixation points.

9. The venous tourniquet of claim 8, wherein the elastic portion or a different portion of the elastic strap has a usage indicator that tears when stretching first occurs.

10. The venous tourniquet of claim 9, wherein the attachment of the second closure part and/or of the elastic portion or of the strap portion, to the constricting strap is brought about at the fixation points by gluing, welding, thermoplastic methods and/or stitching.

11. The venous tourniquet of claim 6, wherein the elastic portion or a different portion of the elastic strap has a usage indicator that tears when stretching first occurs.

12. The venous tourniquet of claim 1, wherein the tension indicator is embodied as an elastic portion on the constricting strap in a stretching direction between two fixation points, having a strap portion of a flexible, inelastic material and spanning a defined excess length relative to the unstressed constricting strap.

13. The venous tourniquet of claim 12, wherein the constricting strap is embodied of a flexible inelastic material, and the strap portion forms an integral part of the constricting strap, and an elastic element forming the elastic portion is attached at the fixation points.

14. The venous tourniquet of claim 13, wherein the constricting strap itself is embodied at least in some portions as an elastic portion, and the strap portion of inelastic material is attached to the elastic portion at the fixation points.

15. The venous tourniquet of claim 1, wherein the tension indicator further comprises an elastic element fixed at opposing ends of the elongation portion and configured to extend during tourniquet use to elongate the elongation portion.

16. The venous tourniquet of claim 1, wherein the tension indicator comprises an elastic element fixed at opposing fixation points along the constricting strap, wherein each fixation point is one of opposing ends of the elongation portion.

17. A venous tourniquet, comprising:
   a constricting strap configured to be placed around a body part, the constricting strap embodied elastically in the circumferential direction or provided with at least one elastic portion, wherein the constricting strap is formed of a plush, tear-resistant nonwoven material with a high tensile strength;
   the constricting strap including a closure device configured to lock when the constricting strap is wrapped tightly around the body part, to form a tightening loop, wherein the closure device comprises a hook-and-loop closure with two closure parts engaging one another in locking fashion, a first closure part of the two closure parts being a surface of the nonwoven constricting strap, and a second closure part of the two closure parts being formed of a portion of material secured to the band material, or the first and the second closure parts being integrated with the band material, and wherein the first closure part is provided with loops and the second closure part is provided with hook elements, configured for catching on the loops; and
   at least one tension indicator comprising an elongation portion of the constricting strap, wherein the elongation portion indicates a state of tension of the constricting strap in such a way that a defined state of tension is apparent to a user, wherein the tension indicator comprises an elastic element fixed at opposing ends of the elongation portion of the constricting strap, and the elongation portion comprises an inelastic excess and/or folded length of the constricting strap with respect to a spacing between two opposing fixation points of the elastic element in an untensed state of the elastic element, wherein the elastic element is configured to reach a maximally stretched position at a defined tension state of the constricting strap corresponding to a pressure of between 10 mm Hg and 25 mm Hg.

18. The venous tourniquet of claim 17, wherein the constricting strap is made from a polyester, polypropylene and/or viscose nonwoven material.

\* \* \* \* \*